(12) United States Patent
Singh et al.

(10) Patent No.: US 7,817,830 B2
(45) Date of Patent: Oct. 19, 2010

(54) LOCATING AN ELONGATED OBJECT IN A THREE-DIMENSIONAL DATA ARRAY

(75) Inventors: Arun Singh, North Wales, PA (US);
Edward Marandola, Gwynedd, PA (US); Omid Kia, North Bethesda, MD (US); Uwe Mundry, Mauldin, SC (US)

(73) Assignee: Imaging Sciences International LLC, Hatfield, PA (US)

( * ) Notice: Subject to any disclaimer, the term of this patent is extended or adjusted under 35 U.S.C. 154(b) by 1130 days.

(21) Appl. No.: 11/437,523

(22) Filed: May 20, 2006

(65) Prior Publication Data

US 2006/0274926 A1 Dec. 7, 2006

Related U.S. Application Data

(60) Provisional application No. 60/682,971, filed on May 20, 2005.

(51) Int. Cl.
*G06K 9/00* (2006.01)
(52) U.S. Cl. .................................................. 382/128
(58) Field of Classification Search ......... 382/128–134; 128/920–930; 250/455–465; 356/39–49; 600/407, 408, 409, 410, 411, 412, 413, 414, 600/424, 425, 426
See application file for complete search history.

(56) References Cited

U.S. PATENT DOCUMENTS

| | | | |
|---|---|---|---|
| 4,661,967 | A | 4/1987 | Nishikawa |
| 4,856,038 | A | 8/1989 | Guenther et al. |
| 5,195,114 | A | 3/1993 | Sairenji et al. |
| 5,214,686 | A | 5/1993 | Webber |
| 5,339,367 | A | 8/1994 | Roth |
| 5,511,106 | A | 4/1996 | Doebert et al. |
| 5,677,940 | A | 10/1997 | Suzuki et al. |

(Continued)

FOREIGN PATENT DOCUMENTS

JP 4144548 5/1992

(Continued)

OTHER PUBLICATIONS

International Search Report and Written Opinion for PCT/US06/19319, mailed Nov. 8, 2007.

(Continued)

*Primary Examiner*—Samir A. Ahmed
*Assistant Examiner*—Atiba O Fitzpatrick
(74) *Attorney, Agent, or Firm*—Michael Best & Friedrich LLP

(57) ABSTRACT

A method and apparatus for locating an elongated object in a three dimensional data array are disclosed. A slice of data generally lengthways of the elongated object is selected. Points on the object in the selected slice are identified. Data including the points are transposed parallel to the slice and transversely to the elongated object to align the points in a direction parallel to the slice and transverse to the elongated object. A current slice is selected that is rotated around the length direction of the object relative to the previously selected slice. The identifying and transposing are repeated to align points on the object in a direction parallel to the current slice and transverse to the elongated object.

23 Claims, 3 Drawing Sheets

U.S. PATENT DOCUMENTS

| | | |
|---|---|---|
| 5,784,429 A | 7/1998 | Arai |
| 6,021,222 A | 2/2000 | Yamagata |
| 6,049,584 A | 4/2000 | Pfeiffer |
| 6,289,074 B1 | 9/2001 | Arai et al. |
| 6,493,415 B1 | 12/2002 | Arai et al. |
| 6,570,953 B1 | 5/2003 | Dobert et al. |
| 6,798,860 B1 | 9/2004 | Hsieh et al. |
| 6,859,555 B1 | 2/2005 | Fang et al. |
| 7,039,156 B2 | 5/2006 | Arai et al. |
| 7,421,059 B2 | 9/2008 | Suzuki et al. |
| 7,460,638 B2 | 12/2008 | Singh et al. |
| 7,499,576 B2 | 3/2009 | Setala |
| 2003/0114756 A1* | 6/2003 | Li .................. 600/437 |
| 2004/0236210 A1 | 11/2004 | Tsai et al. |
| 2004/0249270 A1* | 12/2004 | Kondo et al. ......... 600/425 |

FOREIGN PATENT DOCUMENTS

| | | |
|---|---|---|
| JP | 2001061834 | 3/2001 |
| JP | 3621146 | 2/2005 |

OTHER PUBLICATIONS

Office Action from U.S. Patent Office for U.S. Appl. No. 11/437,525 dated Sep. 27, 2007 (9 pages).

U.S. Appl. No. 11/437,525 Third-Party Submission of Prior Art in Published Application mailed Oct. 3, 2007 (38 pages).

PCT/US6/19320 International Search Report and Written Opinion dated Feb. 11, 2008 (10 pages).

PCT/US2006/019320 International Preliminary Report on Patentability dated Mar. 6, 2008 (2 pages).

Office Action from U.S. Patent Office for U.S. Appl. No. 11/437,526 dated Feb. 26, 2008 (8 pages).

Office Action from U.S. Patent Office for U.S. Appl. No. 11/437,526 dated Sep. 22, 2008 (8 pages).

Office Action from U.S. Patent Office for U.S. Appl. No. 11/437,524 dated Jan. 20, 2010 (10 pages).

* cited by examiner

LOCATING AN ELONGATED OBJECT IN A THREE-DIMENSIONAL DATA ARRAY

CROSS REFERENCE TO RELATED APPLICATIONS

This application claims the benefit of U.S. Provisional Patent Application No. 60/682,971, filed May 20, 2005, which is incorporated herein by reference in its entirety.

This application is related to the following U.S. patent applications which are filed on even date herewith and which are incorporated herein by reference:

Ser. No. 11/437,525 entitled LOCATION OF FOCAL PLANE;

Ser. No. 11/437,524 entitled LOCATION OF CURVED STRUCTURE; and

Ser. No. 11/437,526 entitled PANORAMIC VIEW GENERATOR.

BACKGROUND

The invention relates to locating an elongated object in a three-dimensional array of data, and especially, but not exclusively, to locating an elongated structure in a tomographic imaging dataset. The invention has particular application to locating the nerve canal in x-ray tomographic dental imaging of the mandible or lower jaw of a human or other mammal.

In certain forms of dental surgery, such as implant surgery, it is necessary to drill into the mandible. For secure implantation of, for example, a prosthetic tooth, a deep drilled hole is desirable. However, within the mandible there is a nerve canal containing the neurovascular bundle to the teeth and parts of the face. If the surgeon drills too deeply, and damages the nerve, permanent numbness of portions of the face may result, to the potentially considerable detriment of the patient.

A set of three-dimensional data relating to a property of an object that varies over space within the object may be obtained in various ways. For example, an x-ray image of a target may be obtained by placing the target between a source of x-rays and a detector of the x-rays. In a computed tomography (CT) system, a series of x-ray images of a target are taken with the direction from the source to the detector differently oriented relative to the target. From these images, a three-dimensional representation of the density of x-ray absorbing material in the target may be reconstructed. Other methods of generating a three-dimensional dataset are known, including magnetic resonance imaging, or may be developed hereafter.

From the three-dimensional data, a section in a desired plane may be generated. In planning for dental implant work, the surgeon may display tomograms in planes along and across the mandible, and attempt to identify the nerve canal in the tomograms. However, the contrast of x-ray tomograms is often poor, and the interior of the mandible is formed from bone of comparatively low density. In addition, the nerve canal is not smoothly curved along its length, but undulates irregularly. The nerve may therefore appear in an unexpected place in a transverse section, and may be difficult to follow in a longitudinal section. The nerve may also disappear out of the plane of a longitudinal section regardless of how the section plane is aligned. Consequently, it is not always easy for the surgeon to recognize the mandibular nerve and plan surgery correctly.

There is therefore a hitherto unfulfilled need for a system by which the mandibular nerve can be accurately identified and marked on tomograms of the mandible, enabling the surgeon reliably to avoid the nerve when drilling for implantation, and to assess whether sufficient depth of sound bone is available for a good implant.

SUMMARY

According to one embodiment of the invention, there is provided a method and system for locating an elongated object in a three dimensional data array. A slice of data generally lengthways of the elongated object is selected. Points on the object in the selected slice are identified. Data including the points are transposed parallel to the slice and transversely to the elongated object to align the points in a direction parallel to the slice and transverse to the elongated object. A current slice is selected that is rotated around the length direction of the object relative to the previously selected slice. The identifying and transposing are repeated to align points on the object in a direction parallel to the current slice and transverse to the elongated object.

According to a preferred embodiment of the invention, the data array is a tomographic dataset of a human mandible, and the elongated object is the mandibular nerve or mandibular nerve canal.

By locating the whole, or a substantial part, of the mandibular nerve in the three-dimensional tomographic dataset, and exploiting the fact that the nerve is continuous along its length, the mandibular nerve can be identified with far greater confidence than is attainable when inspecting a single x-ray image or tomogram.

The invention also provides computer software arranged to generate an image in accordance with the method of the invention, and computer-readable media containing such software. The software may be written to run on an otherwise conventional computer processing tomographic data.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION

Reference will now be made in detail to various embodiments of the present invention, examples of which are illustrated in the accompanying drawings.

Figure 1:
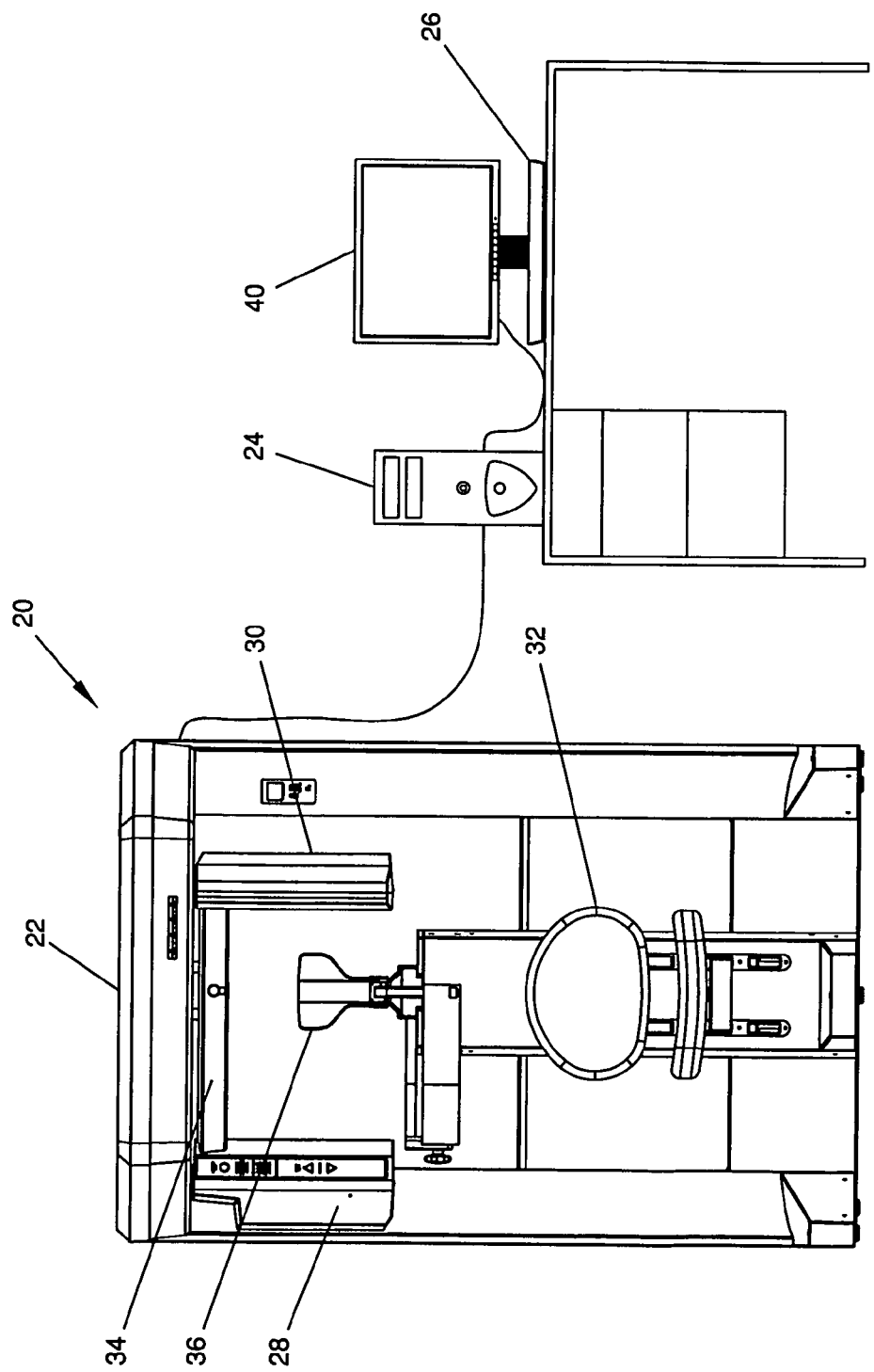
FIG. 1 is a schematic view of apparatus for generating a tomographic image.
Figure 2:
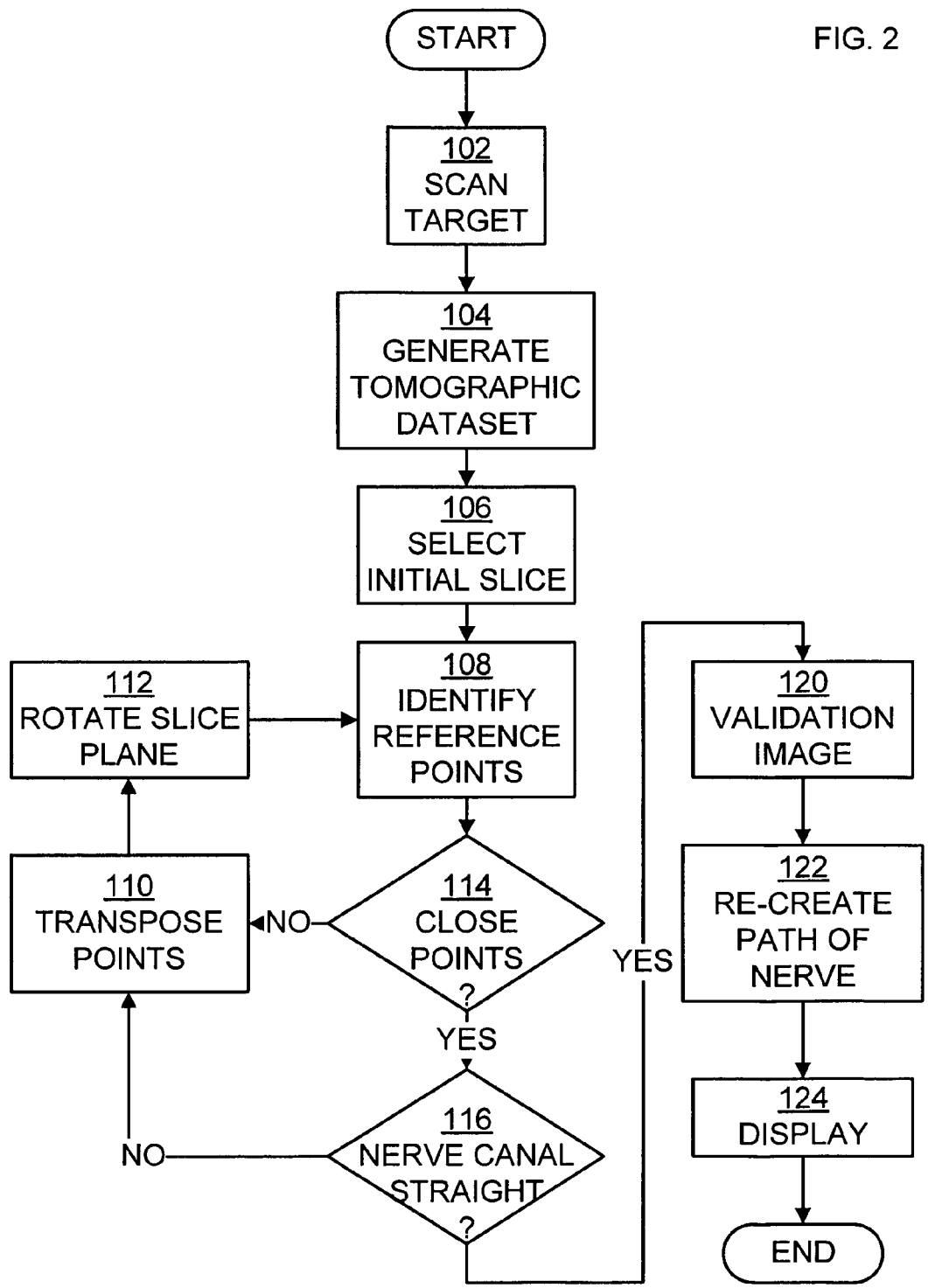
FIG. 2 is a flow chart.

Referring to the drawings, and initially to FIGS. 1 and 2, one form of tomographic apparatus according to an embodiment of the invention, indicated generally by the reference numeral 20, comprises a scanner 22 and a computer 24 controlled by a console 26. The scanner 22 comprises a source of x-rays 28, an x-ray detector 30, and a support 32 for an object to be imaged. In an embodiment, the scanner 22 is arranged to image the head, or part of the head, of a human patient (not shown), especially the jaws and teeth. The support 32 may then be a seat with a rest or restrainer 36 for the head or face (not shown) of the patient. The x-ray source 28 and detector 30 are then mounted on a rotating carrier 34 so as to circle round the position of the patient's head, while remaining aligned with one another. In step 102, the x-ray detector 30 then records a stream of x-ray shadowgrams of the patient's head from different angles. The computer 24 receives the x-ray image data from the scanner 22, and in step 104 calculates a 3-dimensional spatial distribution of x-ray density.

The imaging of the patient's head and calculation of the spatial distribution may be carried out by methods and apparatus already known in the art and, in the interests of conciseness, are not further described here. Suitable apparatus is available commercially, for example, the i-CAT Cone Beam 3-D Dental Imaging System from Imaging Sciences International of Hatfield, Pa.

Figure 3:
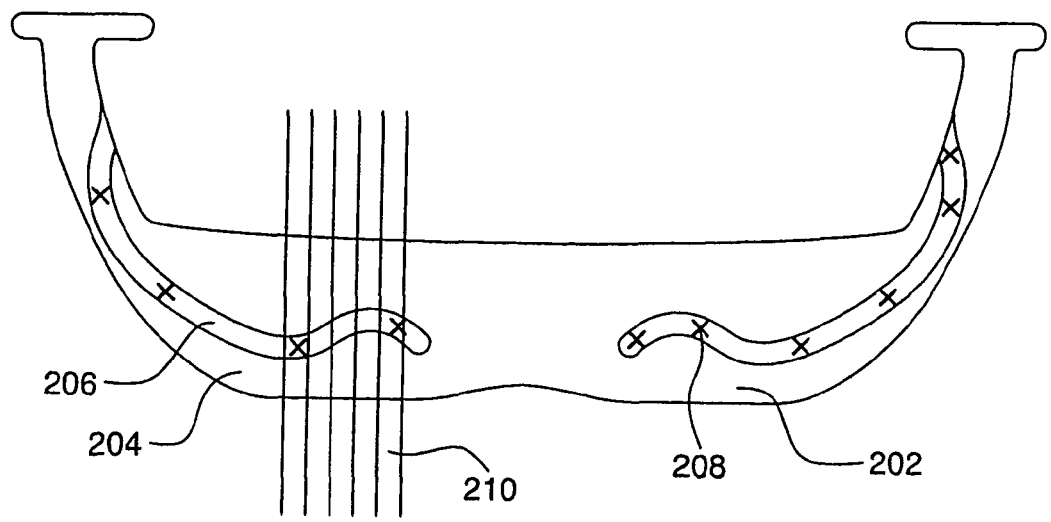
FIG. 3 is a somewhat schematic panoramic view of a mandible, showing the nerve canals.

In step 106, an initial slice 202 through the tomographic dataset is selected. As shown in FIG. 3, the initial slice 202 is a "curved slice" similar to a synthesized panoramic view of the mandible. That is to say, the initial slice is formed from vertical (relative to the normal standing or sitting position of a human patient) columns 210 of voxels passing through a line that follows the curve of the mandible 204. (In the interests of clarity, only some of the columns 210 are marked in FIG. 3.) For other species, the operator may select an appropriate orientation, either by positioning the patient for scanning, or by manipulation of the tomographic data. The slice may be selected by a human operator on the display 40 of the console 26, or may be selected automatically by the computer 26 if the computer is programmed to conduct pattern recognition on the tomographic dataset and to locate the mandible. Great precision in choosing the initial slice is not required, since the mandibular nerve is not straight, and will cross any reasonable curved slice. However, precise knowledge of what initial slice has been chosen may be helpful in the next step.

In FIG. 3, the initial slice 202 is shown "developed" or unrolled into a flat surface, like a panoramic x-ray image. This is a useful arrangement where the slice 202 is displayed on the display 40 for a human operator. The initial slice 202 is selected so that the nerve canal 206 is visible along its length. The initial slice 202 may be a thick slice, several voxels in extent in a direction perpendicular to the plane of the image in FIG. 3, and positioned relative to the mandible 204 so that at least most of the nerve canal 206 is in the slice. Alternatively, the initial slice 202 may be a thin slice, possibly only a single voxel thick, positioned so that the nerve canal 206 repeatedly crosses the initial slice.

Figure 4:
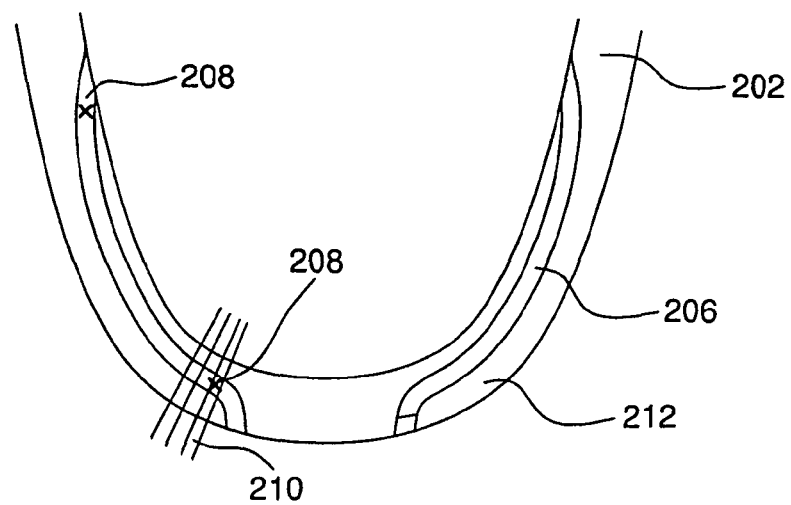
FIG. 4 is a somewhat schematic top view of a mandible, showing the nerve canals.

In the interests of linguistic simplicity, the description of FIGS. 2 to 4 describes tracing the mandibular nerve 206 as if the mandibular nerve appears in the dataset as a nerve line that occupies one voxel in any slice transverse to the length of the nerve, and thus occupies a single pixel in any transverse section image. In a practical embodiment, the nerve and nerve canal will appear as a "bull's eye" pattern several voxels across, and may be recognized by pattern recognition of a transverse slice of the dataset centered on the voxel where the notional nerve line intersects the transverse slice.

In step 108, a number of reference points 208 of the nerve canal 206 are identified in the initial slice 202. Because the position of the mandibular nerve is known in general terms, if a suitable initial slice is chosen some assumptions can be made as to where the mandibular nerve will be found in the initial slice. The points 208 may be points where the mandibular nerve 206 crosses the initial slice 202, or may be distinctive points of the nerve within the slice 202. The operator may identify the points 208 visually on the display 40, and may identify the points to the computer 24 by positioning a cursor or pointer on the display 40. Alternatively, the initial points may be identified by pattern recognition. The effectiveness of computer pattern recognition may be limited since at times the nerve canal may be barely visible even to the human eye. Therefore, where a skilled human is available, he or she may be preferred. However, the quality of computer methods is constantly improving, and may become better than the human eye. The points 208 are chosen because they are identifiable with a high degree of certainty, and are spaced out along the length of the nerve canal, so that the distance between any two adjacent points 208 is not too long. The minimum number of points needed, or the maximum spacing between adjacent points, very much depends upon the extents of the canal. If the canal does not undulate much, just a few points—maybe 4 or 6 per side—may be sufficient. On the other hand, if the canal undulates a lot, many more points may be needed. Where a suitable set of initial reference points 208 cannot be identified with sufficient confidence, the computer may loop back to step 106 and select a different initial slice, in which the initial points may be more easily recognized.

In step 110, the columns 210 of voxels containing the points 208 are transposed or shifted up or down so that the points 208 are in a straight, horizontal line in the view shown in FIG. 3. The columns 210 that are between points 208 may be transposed by a linear interpolation on each section, or by a more sophisticated interpolation, for example, a cubic spline or the like. Alternatively, sub-sections of the nerve canal may be detected algorithmically and shifted accordingly. The points 208 are not aligned perpendicular to the plane of FIG. 3. Where the slice 202 is thick enough to contain the entire nerve canal 206, the shifting of each column 210 is applied to a row of columns that extends perpendicular to the plane of the view in FIG. 3 for the thickness of the slice. Where the slice 202 is thinner, the columns of voxels in front and behind the slice are shifted correspondingly, so that the whole nerve line is aligned.

In step 112, the plane of view is rotated, for instance, 90° about the line of points 208, so that the nerve canal 206 is presented in a top view slice 212. Because the top view slice 212 is based on the transposed dataset generated in step 110, the voxels of the nerve 206 are concentrated in a top view slice that may be only one or a few voxels thick, in a vertical position determined by the shifting process. Consequently, the top view slice 212 may be a thinner slice than the frontal slice 208 and still contain the entire nerve canal 206. However, the shifting in step 110 was perpendicular to the top view slice 212 and thus did not affect the positions of the nerve voxels along or across the plane of the top view slice. As shown in FIG. 4, the mandible with the nerve canal is presented in its natural curved shape, but it may instead be presented straightened out, corresponding to the "developed" panoramic image in FIG. 3.

The process then returns to step 108 to identify a set of reference points 208 in the newly presented image. The first time the plan view of FIG. 4 is viewed, the same points 208 as in FIG. 3 may be used, or new points that are easily identified in the plan view may be used. The process then proceeds to step 110 to move the newly identified reference points 208 into a straight line. In this iteration of step 110, the columns 210 of voxels that are shifted to move the points 208 are radial columns in the plane of FIG. 4, together with enough corresponding radial columns just above and below the plane of FIG. 4 to ensure the entire nerve canal 206 is being shifted.

Steps 112, 108, and 110 are then repeated as often as necessary. At each iteration, the line of the nerve canal 206 in the images becomes more nearly straight, and easier to identify, so the reference points 208 can be found closer and closer together, until it is determined in step 114 that the reference points 208 are closer than the scale of the undulations in the nerve canal 206, so that a straight alignment of the points 208 reliably indicates a straight alignment of the whole nerve canal. It is then determined in step 116 whether the nerve canal 206 is in fact substantially straight both in the frontal view plane 202 of FIG. 3 and in the top view plane 212 of FIG. 4, and/or optionally in other arbitrary rotation views.

In step 120 the computer 24 verifies that the mandibular nerve 206 has been correctly traced. This may be done by displaying to a human operator the final forms of the frontal slice 202 and the top view slice 212, which should have the entire mandibular nerve 206 displayed in a straight line, or in a smooth curve in FIG. 4, along the slice plane. Alternatively, a pattern recognition routine within the computer 24 may review the transposed mandibular nerve and nerve canal, centered on the straightened nerve 206. Verifying by pattern recognition the presence of the straightened nerve in the transposed dataset is a computationally comparatively simple process.

In step 122, the computer 24 re-creates the original path of the mandibular nerve by working back from the final transposed path of the nerve 206 and a record of the amount and direction of transposition of each nerve voxel. In step 124, the re-created path of the nerve is then superimposed on the original tomographic dataset, and displayed to a human user. The re-created path may be displayed by highlighting appropriate pixels in the display of the tomographic dataset. For example, the nerve may be shown by brightly colored pixels marking the nerve line. Depending on the size and resolution of the image, for example, a single pixel or a cluster of pixels around the nerve line may be highlighted. The re-created path may be recorded by editing a copy of the tomographic dataset to highlight the appropriate voxels. Alternatively, the re-created path may be stored in a separate file, and combined with the tomographic dataset when a display image is generated.

Where the computer 24 in step 108 fails to identify a sufficient set of reference points 208 for the next iteration, various additional actions may be taken to recover. For example, the computer 24 may use a more computationally intensive process to recognize reference points, or may use a lowered threshold of confidence that a valid reference point 208 has been identified. For example, the computer may refer to a human operator to make additional selections.

If the recovery is successful, the computer proceeds to step 110, and continues the iterative nerve straightening process. If the recovery is not successful, the computer may still proceed to step 120 and generate a validation image to be reviewed by a human operator, to decide whether the imperfectly straightened nerve path actually provides sufficient information to be useful for a specific surgical or other operation.

Various modifications and variations can be made in the present invention without departing from the spirit or scope of the invention. Thus, it is intended that the present invention cover modifications and variations of this invention provided they come within the scope of the appended claims and their equivalents.

For example, FIG. 1 shows that the computer 24 on which the process of FIG. 2 is running is connected to the scanner 22. A single computer 24 may both control the scanner 22 and run the process of FIG. 2. Alternatively, part or all of the process of FIG. 2 may be carried out on a separate computer. The data from the scanner 22 may be transferred from computer to computer in a convenient format, for example the DICOM format, at a convenient stage of the process. The data may, for example, be transferred directly from computer to computer or may, for example, be uploaded to and downloaded from a storage server.

What is claimed is:

1. A method of locating an elongated object in a three dimensional data array, the method comprising:
    selecting a first slice of data through the three-dimensional array, the first slice of data being generally lengthways of the elongated object;
    identifying points on the elongated object in the first slice of data;
    transposing columns of voxels in the first slice of data in a direction parallel to the first slice of data and transverse to the elongated object to align the points in a straight line parallel to the first slice of data, the columns being parallel to the first slice of data and transverse to the elongated object;
    rotating the three-dimensional data array around a length direction of the elongated object to obtain a second slice of data;
    identifying additional points on the elongated object in the second slice of data;
    transposing columns of data in the second slice of data in a direction parallel to the second slice of data and transverse to the elongated object to align the previously identified points and the additional points in a substantially straight line parallel to the second slice of data; and
    repeating the acts of rotating, identifying, and transposing until a minimum number of points are aligned along the straight line.

2. The method according to claim 1, further comprising repeating the selecting, identifying and transposing until the substantially straight line of points conforms to a desired line to a desired degree of precision.

3. The method according to claim 1, further comprising recording the transpositions made, and calculating from the transpositions the position of the object in the untransposed three-dimensional data array.

4. The method according to claim 3, further comprising displaying sections through the untransposed three-dimensional data array with the calculated position of the elongated object superimposed.

5. The method according to claim 4, wherein the three-dimensional data array is data of at least part of a human or animal, and the elongated object is a desired anatomical feature.

6. The method according to claim 5, wherein the part of the human or animal comprises at least part of a mandible, and the desired anatomical feature is the mandibular nerve.

7. The method according to claim 1, wherein the three-dimensional data array is a tomographic dataset.

8. The method according to claim 7, wherein the tomographic dataset includes tomographic data of a mandible, and the elongated object includes data points representing the mandibular nerve.

9. The method according to claim 8, wherein the first selected slice is generally upright relative to the upright position of the person whose mandible is represented, and extends along the mandibular arch.

10. The method according to claim 8, wherein the first selected slice is generally horizontal relative to the upright position of the person whose mandible is represented.

11. The method according to claim 1, further comprising carrying out the identifying and transposing using a computer.

12. The method according to claim 1, further comprising carrying out the transposing using a computer, generating a display of the currently selected slice on a visual display unit using a computer, and carrying out the identifying on the visual display unit.

13. A three dimensional data array including an elongated object and comprising data determined by a method according to claim 1 indicating the position of the elongated object within the data array.

14. An apparatus comprising a computer programmed to carry out the method of claim 1.

15. An apparatus according to claim 14, further comprising a tomographic scanner, and arranged to generate the three dimensional data array from data generated by the scanner so as to represent an object scanned by the scanner.

16. An apparatus comprising a processor and a computer-readable memory, the computer-readable memory storing instructions that, when executed by the processor, cause the apparatus to:
   select a first slice of data through the three-dimensional array, the first slice of data being generally lengthways of an elongated object;
   identify points on the elongated object in the first slice of data;
   transpose columns of voxels in the first slice of data in a direction parallel to the first slice of data and transverse to the elongated object to align the points in a straight line parallel to the first slice of data the columns being parallel to the first slice of data and transverse to the elongated object;
   rotate the three-dimensional data array around a length direction of the elongated object to obtain a second slice of data;
   identify additional points on the elongated object in the second slice of data;
   transpose columns of data in the second slice of data in a direction parallel to the second slice of data and transverse to the elongated object to align the previously identified points and the additional points in a substantially straight line parallel to the second slice of data; and
   repeat the acts of rotating, identifying, and transposing until a minimum number of points are aligned along the straight line.

17. The apparatus according to claim 16, wherein the instructions, when executed by the processor, cause the apparatus to repeat the selecting, identifying and transposing until the substantially straight line of points conforms to a desired line to a desired degree of precision.

18. The apparatus according to claim 16, wherein the instructions, when executed by the processor, cause the apparatus to record the transpositions made, and calculate from the transpositions the position of the object in the untransposed three-dimensional data array.

19. The apparatus according to claim 16, wherein the instructions, when executed by the processor, cause the apparatus to display sections through the untransposed three-dimensional data array with the calculated position of the elongated object superimposed.

20. A method of locating an elongated object in a three-dimensional data array, comprising:
   selecting a slice of data generally lengthways of the elongated object;
   identifying points on the elongated object in the selected slice;
   transposing data including the points parallel to the slice and transverse to the elongated object to align the points on the elongated object in a direction parallel to the slice;
   selecting a current slice rotated around a length direction of the elongated object relative to the previously selected slice; and
   repeating the identifying and transposing to align the points on the elongated object in a direction parallel to the current slice,
   wherein the three-dimensional data array is a tomographic dataset, the tomographic dataset is tomographic data of a mandible, and the elongated object is data points representing a mandibular nerve.

21. The method according to claim 20, wherein the first selected slice is generally upright relative to an upright position of a person whose mandible is represented, and extends along a mandibular arch.

22. The method according to claim 20, wherein the first selected slice is generally horizontal relative to an upright position of a person whose mandible is represented.

23. A method of locating an elongated object in a three-dimensional data array, comprising:
   selecting a slice of data generally lengthways of the elongated object;
   identifying points on the elongated object in the selected slice;
   transposing data including the points parallel to the slice and transverse to the elongated object to align the points on the elongated object in a direction parallel to the slice;
   selecting a current slice rotated around a length direction of the elongated object relative to the previously selected slice;
   repeating the identifying and transposing to align the points on the elongated object in a direction parallel to the current slice;
   recording the transpositions made;
   calculating from the transpositions the position of the object in the untransposed data array; and
   displaying sections through the untransposed data array with the calculated position of the object superimposed,
   wherein the data array is data of at least part of a human or animal, and the object is a desired anatomical feature, and
   wherein the part of the human or animal comprises at least part of a mandible and the desired anatomical feature is the mandibular nerve.

* * * * *